United States Patent [19]

Eschwey et al.

[11] 4,329,381
[45] May 11, 1982

[54] METHOD FOR PROVIDING CORROSION RESISTANCE TO METAL OBJECTS

[75] Inventors: Helmut Eschwey, Odenthal, Fed. Rep. of Germany; Joachim Galinke, deceased, late of Langenfeld, Fed. Rep. of Germany; Renate Galinke, nee Jansen, heir, Langenfeld, Fed. Rep. of Germany; Heinrich Linden, Düsseldorf-Holthausen, Fed. Rep. of Germany; Bernd Wegemund, Haan, Fed. Rep. of Germany; Norbert Wiemers, Monheim-Baumberg, Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 11,696

[22] Filed: Feb. 12, 1979

[30] Foreign Application Priority Data

Feb. 23, 1978 [DE] Fed. Rep. of Germany ....... 2807698
Jun. 3, 1978 [DE] Fed. Rep. of Germany ....... 2824508

[51] Int. Cl.³ .................................................. C09D 5/08
[52] U.S. Cl. ................................. 427/386; 106/14.37; 106/14.38; 252/391; 427/388.1; 428/470
[58] Field of Search ...................... 424/245; 106/18.32, 106/292, 14.37, 14.38; 260/45.75 W; 427/386, 388.1; 428/470

[56] References Cited

U.S. PATENT DOCUMENTS

| | | | |
|---|---|---|---|
| 2,727,879 | 12/1955 | Vincent | 260/45.75 W |
| 3,436,364 | 4/1969 | Logemann et al. | 260/45.75 W |
| 3,535,300 | 10/1970 | Gable | 260/45.85 N |
| 3,929,794 | 12/1975 | McCrae | 106/292 |
| 3,940,482 | 2/1976 | Grand | 424/245 |

Primary Examiner—Lorenzo B. Hayes
Attorney, Agent, or Firm—Hammond & Littell, Weissenberger and Muserlian

[57] ABSTRACT

Method for providing corrosion protective coatings for metal surfaces. The coatings contain conventional coating components to which are added at least one zinc or lead salt of five- or six-membered heterocyclic compounds substituted by at least one hydroxyl or mercapto group and the ring includes at least one nitrogen atom and at least two conjugated double bonds, of which at least one has the formation.

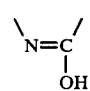

(I)

or

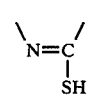 (II)

as corrosion inhibitors.

7 Claims, No Drawings

METHOD FOR PROVIDING CORROSION RESISTANCE TO METAL OBJECTS

FIELD OF THE INVENTION

This invention relates to corrosion protective coatings for metal surfaces, particularly, for iron which coatings contain, in addition to the other customary components, zinc and/or lead salts of nitrogen-containing heterocyclic organic compounds as corrosion inhibitors.

BACKGROUND OF THE INVENTION

In order to inhibit the metal corrosion process or to prevent it as completely as possible, metal surfaces are conventionally coated with primers or lacquers which contain corrosion inhibitors as the active components. It has been known for a long time to use such compounds as zinc potassium chromate, zinc tetrahydroxichromate, strontium chromate, barium chromate, or red lead oxide as corrosion inhibitors in corrosion protective coatings. Recently, however, the attention of the manufacturers of such coatings has been directed to the environmental behavior of such corrosion inhibitors. As a result, such time-tried inhibitors as zinc potassium chromate have been increasingly replaced by more environmentally acceptable corrosion inhibitors such as zinc phosphate.

The corrosion inhibiting property of zinc phosphate is based on the formation of protective layers in anionic pH ranges. The protective electrochemical reactions of zinc potassium chromate, do not take place with zinc phosphate, so that, until now, a combination of zinc phosphate with at least one electrochemically active corrosion protective pigment has always been recommended (Deutsche Farben Zeitschrift (Defazet) 29 (1975) 13–17).

Such electrochemically active corrosion inhibiting compounds are, for example, zinc and/or lead salts of 3-nitrophthalic acid, 4-nitrophthalic acid, 5-nitroisophthalic acid, or mononitroterephthalic acid, as are described in the German published patent applications DE-AS 22 04 985 and DE-AS 25 02 781. While such substances show an improved corrosion inhibiting effect (corrosion protection value) as compared with the conventional inhibitors, it appears that, when applied in the usual binder formulations, the coating materials such as paints and lacquers containing such corrosion inhibitors exhibit poor stability with respect to their sedimentation and the formation of solid agglomerated sediments which considerably complicate the practical application of such coating materials.

OBJECTS OF THE INVENTION

It is an object of the present invention to provide corrosion inhibitors for corrosion protective coatings which effect as large a corrosion inhibition as possible and do not have a deleterious effect on the sedimentation stability of the compounds and possess good dispersibility.

Another object of the present invention is the development of compositions for coating metal surfaces with corrosion protective coatings which contain a corrosion-protecting amount of at least one zinc and/or lead salt of a five- or six-membered nitrogen-heterocyclic compound substituted by at least one hydroxyl or mercapto group which contains at least one ring-nitrogen and at least two conjugated double bonds, of which at least one has the formation.

(I)

or

(II)

in a film-forming vehicle suitable for application to metals.

These and other objects of the invention will become more apparent as the description thereof proceeds.

DESCRIPTION OF THE INVENTION

The compositions of this invention are therefore improved corrosion protective coatings for metal surfaces based on conventional coating components as well as zinc and/or lead salts of organic compounds where the improvement specifically includes the zinc and/or lead salts of five- or six-membered ring heterocyclic compounds substituted with at least one hydroxyl or mercapto group, which contain in their ring at least one nitrogen atom and at least two conjugated double bonds, of which at least one has the formation.

(I)

or

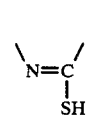
(II)

We have found, to our surprise, that the zinc and/or lead salts of such heterocyclic compounds demonstrate, in conventional binder formulations for corrosion protective coatings, excellent corrosion inhibiting effects. Further, coating compositions including such salts have excellent stability with respect to their sedimentation behavior.

In addition, such corrosion inhibitor compounds have further advantages, compared to the electrochemically-active inhibitors known to the state of the art. The extremely low water-solubility of the salts according to the invention (the solubility of the zinc salts in water (20° C.) is 0.1% or lower, the solubility of the lead salts is 0.01% or lower), provides an improved stability and extended protection of the corrosion protective coatings or lacquer films prepared with them, since these salts cannot easily be washed out of the lacquer film when formed. This minimal solubility of the inhibitors, according to the invention, is a positive advantage with respect to their environmental behavior under leaching conditions. The drained waters have much lower concentrations of toxic materials.

Among the five-membered heterocyclic compounds that form the zinc and/or lead salts according to this invention, there may be mentioned the following as examples:

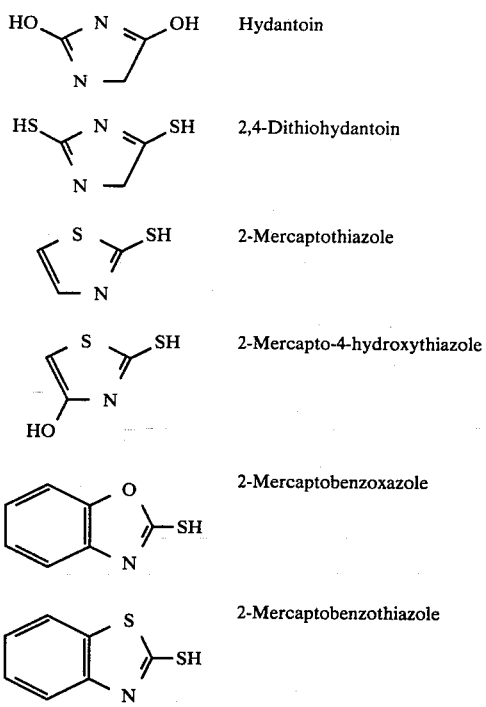

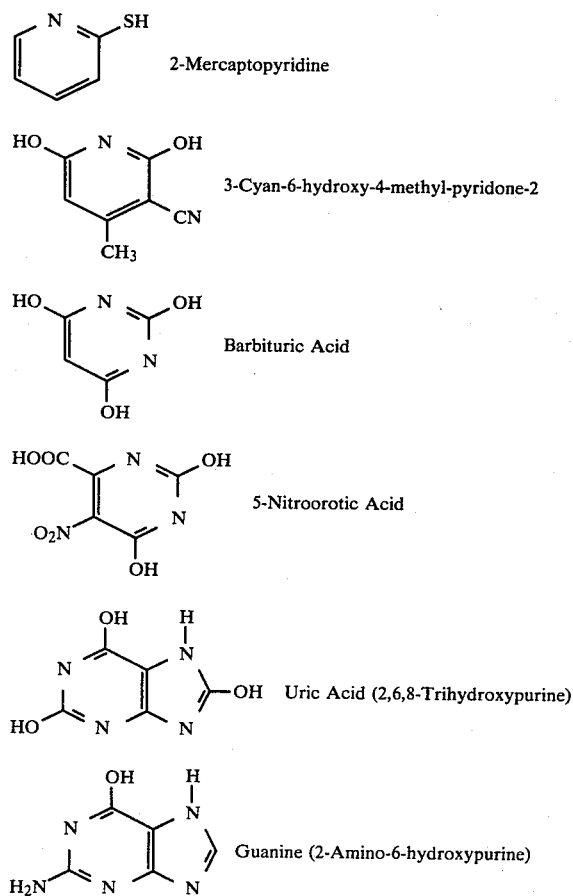

As examples for corresponding six-atom heterocyclic compounds, the following should be named:

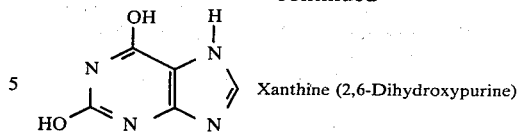

As is apparent from the above, compounds suitable for heterocyclic compound inhibitors, according to this invention, may contain two nitrogen atoms in the ring or additional ring hetero-atoms. Heterocyclic compounds with one or more nuclei, as well as compounds that contain additional substituents in addition to the one or more hydroxyl and/or mercapto groups, are also suitable.

The effective corrosion inhibitors, in the sense of the invention, can therefore be considered, as an example, the zinc or lead salts of the following heterocycles: pyrroles, imidazoles, pyrazoles, pyridines, pyrazines, pyrimidines, pyridazines, isoindoles, indazoles, purines, quinolines, isoquinolines, quinazolines, phenazines, oxazoles, isooxazoles, thiazoles, benzothiazoles, benzimidazoles, benzoxazoles, and other heterocyclic moieties, provided that they contain at least one hydroxy or mercapto group in the structural configuration I and II, as defined above. It is, of course, understood that some of these moieties may exist in their keto-forms however, for salt formation with zinc or lead, only the corresponding enol form is suitable. The same is true for the mercapto group.

Of special importance and preferred in the sense of the invention, are the zinc or lead salts of the mercaptobenzothiazoles as well as the mercaptopyridines, since excellent corrosion protective values have been achieved with corrosion protective coatings based on these salts, and, particularly, since no sediment is formed in corrosion protective coating compositions containing these salts even over extended periods of storage.

Also preferred in the sense of this invention are the zinc and lead salts of s-triazine derivatives with single- or multiple-ring nuclei which contain at least one hydroxyl or mercapto group on the triazine ring.

Examples of single-ring s-triazine derivatives which form zinc and/or lead salts in the sense of the invention include:
cyanuric acid (2,4,6-trihydroxy-s-triazine),
monothiocyanuric acid (2,4-dihydroxy-6-mercapto-s-triazine),
dithiocyanuric acid (2-hydroxy-4,6-dimercapto-s-triazine),
trithiocyanuric acid (2,4,6-trimercapto-s-triazine),
Allantoxaidine (2,4-dihydroxy-s-triazine).

The triazine ring may contain in addition to hydroxy or mercapto groups, further substituents. Corresponding single-ring nucleus zinc and/or lead salt-forming compounds are, for example:
ammelide (2,4-dihydroxy-6-amino-s-triazine),
monothioammelide (2-hydroxy-4-mercapto-6-amino-s-triazine),
dithioammelide (2,4-dimercapto-6-amino-s-triazine),
ammeline (2-hydroxy-4,6-diamino-s-triazine),
thioammeline (2-mercapto-4,6-diamino-s-triazine),
acetothioguanide (2-mercapto-4-amino-6-methyl-s-triazine),
acetoguanamide (2-4-dihydroxy-6-methyl-s-triazine), o-carboxybenzoguanide (2-hydroxy-4-amino-6-(o-carboxyphenyl)-s-triazine),
oxonic acid (2,4-hydroxy-6-carboxy-s-triazine),
2-hydroxy-4,6-dimethoxy-s-triazine,
2,4-hydroxy-6-(p-nitrophenyl)-s-triazine, and
2,4-dihydroxy-6-allyloxy-s-triazine.

In addition to the above exemplified single-ring nucleus s-triazine derivatives, multinucleic s-triazine derivatives, as long as they contain at least one hydroxyl or mercapto group per triazine ring, can also be considered for the formation of zinc and/or lead salts, according to the invention. Among these are, for example, the oligomeric condensation products of ammeline or thioammeline with formaldehyde, or, also, oligomers or polymers or thiocyanuric acid linked over disulfide bridges.

Also zinc and/or lead salts of polynuclear condensed s-triazine ring systems with hydroxyl and/or mercapto groups as, for instance, cyameluric acid (2,5,8-trihydroxy-tri-s-triazine), are also within the ambit of the corrosion inhibitors, according to this invention.

Of special importance, in the sense of the invention, are also the zinc and/or lead salts of cyanuric and thiocyanuric acid. These salts exhibit excellent corrosion protection values when compounded as anticorrosion coating compositions even over long periods of storage.

The coatings, according to this invention, are usually at least 5 $\mu$m in thickness but, preferred, are coatings in the range 10 to 100$\mu$ and containing the zinc, lead or zinc-lead salts as defined.

The following Examples are illustrative of the practice of the invention without being limitative.

EXAMPLES

Preparation of the zinc and/or lead salts

The preparation of the zinc and/or lead salts of the above-mentioned s-triazine derivatives is easily accomplished by different methods. In the following, these methods are illustrated based on cyanuric acid.

Preparative method 1:
Lead and/or zinc carbonate is reacted with cyanuric acid in boiling water. The corresponding metal cyanurates are formed with evolution of carbon dioxide.

Preparative method 2:
Lead and/or zinc nitrate, chloride, or acetate in aqueous solution is reacted at room temperature with an aqueous solution of trisodium or tripotassium cyanurate. The appropriate zinc or lead cyanurate precipitates from the aqueous solution.

Preparative method 3:
Zinc and/or lead oxide is reacted with cyanuric acid in boiling water, preferably in the presence of a small amount of acetic acid as catalyst. The corresponding metal cyanurates are formed.

The preparation of other zinc or lead salts with other moieties is exemplified by their preparation utilizing mercaptobenzothiazole as a representative reactant.

Preparative method 4:
Lead or zinc carbonate is reacted with mercaptobenzothiazole in boiling water. The corresponding zinc or lead salts of mercaptobenzothiazole are formed with evolution of carbon dioxide.

Preparative method 5:
Lead or zinc nitrate, chloride, or acetate is treated, in aqueous solution at room temperature, with an aqueous solution of the sodium or potassium salt of mercaptobenzothiazole. The corresponding zinc or lead salts of mercaptobenzothiazole precipitate from the aqueous solution.

Preparative method 6:
Zinc or lead oxide is reacted with mercaptobenzothiazole in boiling water, preferably, in the presence of a small amount of acetic acid as catalyst. The corresponding zinc or lead salts of mercaptobenzothiazole are formed.

The salts according to the invention are easily incorporated by mixing with conventional binder formulations to prepare the corrosion protective coating compositions of this invention. Generally, small amounts of these salts suffice to obtain the described anti-corrosive effects; i.e., the salts are added to the binders in amounts of from 0.5% to 10% by weight, preferably 1% to 3% by weight, based on the total formulation. Suitable binders for such primer lacquer compositions are the resins conventionally used for such purposes, dissolved or emulsified and dispersed in suitable solvent systems and treated with the usual pigments and fillers used in such compositions.

The following examples demonstrate the effectiveness of the corrosion protective compositions and the resultant coatings according to the invention, with regard to the corrosion protective values (CV) obtained with them, as well as with regard to the improved dispersion of these novel agents in such lacquers. As a basis for comparison, the compositions, according to this invention, were compared with compositions that contained zinc and zinc/lead salts of nitroisophthalic acid, as well as also composition containing zinc potassium chromate or zinc phosphate, as the corrosion inhibitors.

The following testing methods were used to obtain the values reproduced in the Examples:

(A) Corrosion Resistance Testing

The corrosion protective coatings prepared according to each Example were applied on rustfree, degreased steel sheets (150×70×1 mm) by a lacquer-film centrifugal device (mfg. by Erichsen, Germany, type 334/II). The resulting film thickness was standardized to measure between 30 and 33 $\mu$m. After drying, the lacquer films so formed for 2 hours at 60° C., then 8 days at room temperature, two of the steel sheets, each coated with the corrosion protective coating, were subjected to the salt-spray test according to ASTM B 117-64 (continuous spray with a 5% sodium chloride solution at 35° C.) for 200 hours for each corrosion inhibitor composition tested.

One of the test sheets was unmarked, the other was provided, prior to the salt-spray test, with a so-called Andreas cross (Andreas cross=cross cut with a blade of 0.1 mm) through the lacquer film to the substrate.

Two additional coated steel sheets, per each corrosion inhibitor composition under test, were subjected to the Kesternich test according to DIN 50 018 without Andreas cross for the duration of 12 cycles (1 cycle=8 hours at 40° C. in a humid atmosphere containing 0.2 liter sulfur dioxide; followed by an additional 16 hours without load). The stressed test sheet evaluation was based on a rust degree scale according to DIN 53 210. The corrosion protection value (CV) was then calculated according to the method described by Ruf (Farbe and Lack 75 (1969) 943-949) from the results so obtained.

(B) Sedimentation Behavior

To test the sedimentation behavior of the pigments, that is, the corrosion inhibitors in the compositions of this invention, 250 ml wide-neck glass flasks were filled with samples of the corrosion protective coating compositions described in the Examples. By careful manual probing with a 3 mm wide steel spatula, the structure of the sediment, in question, was determined at regular intervals. The rating of the structure of the sediment was based on an evaluation scale of 0 to 4.

This evaluation scale was based on the following key:

| Number | Sediment | Is the pigment stirrable? | Is the lacquer fit for practical application? |
|---|---|---|---|
| 0 | none | — | yes |
| 1 | slight | easily | yes |
| 2 | moderate | moderately | conditionally |
| 3 | strong | difficult | barely |
| 4 | very strong | no, cemented | no |

The following Examples describe the preparation of coating composition according to this invention and also describe and evaluate the results obtained with coating films prepared therewith. In addition, comparison is made with representative prior art materials.

EXAMPLE 1

Composition of the binder formulation:

| Parts by Weight | |
|---|---|
| 34.0 | short oil, resin-modified alkyd resin with 44% linseed oil/wood oil, 60% solution in xylene |
| 9.0 | xylene |
| 5.6 | benzine, b.p. 145° to 200° C. |
| 2.3 | ethylene glycol ethyl ether |
| 2.3 | Decalin ® |
| 0.2 | calcium naphthenate, 4% Ca |
| 0.4 | cobalt napthhenate, 6% Co |
| 0.1 | lead naphthenate, 24% Pb |
| 0.3 | methyl ethyl ketoxime |
| 6.8 | titanium dioxide, Rutile |
| 4.5 | micro talc |
| 23.7 | barium sulfate |
| 8.5 | zinc phosphate |
| 97.7 parts (by weight) | Lacquer base |

To each 97.7 parts of this lacquer base were added 2.3 parts by weight each of the corrosion inhibitors tested. The Examples 1.1 to 1.12 are the salts according to the invention. Examples 1.13 to 1.16 contain as corrosion inhibitors, compounds according to the state of the art. In Example 1.16, zinc phosphate was present from the basic composition without any additional inhibitor.

| Example | Corrosion Inhibitor | CV in % | Sediment 3 days | after-21 days |
|---|---|---|---|---|
| 1.1 | lead salt of mercapto-pyridine (44.0% Pb) | 95 | 0 | 0 |
| 1.2 | zinc salt of mercapto-pyridine (22.6% Zn) | 89 | 0 | 0 |
| 1.3 | lead salt of 3-cyano-6-hydroxy-4-methylpyridone-2 (56.4% Pb) | 88 | 0 | 0 |
| 1.4 | zinc salt of 3-cyano-6-hydroxy-4-methylpyridone-2 (30.2% Zn) | 80 | 0 | 0 |
| 1.5 | lead salt of barbituric acid (64.5% Pb) | 88 | 0 | 0 |
| 1.6 | zinc salt of barbituric acid (35.2% Zn) | 78 | 0 | 0 |
| 1.7 | lead salt of 5-nitroorotic acid (57.9% Pb) | 90 | 0 | 0 |
| 1.8 | zinc salt of 5-nitroorotic acid (28.8% Zn) | 81 | 0 | 0 |
| 1.9 | lead salt of hydantoin (56.9% Pb) | 83 | 0 | 0 |
| 1.10 | zinc salt of hydantoin (40.0% Zn) | 75 | 0 | 0 |
| 1.11 | lead salt of mercapto-benzothiazole (37.3% Pb) | 96 | 0 | 0 |
| 1.12 | zinc salt of mercapto-benzothiazole (16.4% Zn) | 88 | 0 | 0 |
| 1.13 | zinc salt of 5-nitro-isophthalic acid (44.1% Zn) | 73 | 2 | 4 |
| 1.14 | zinc/lead mixed salt of 5-nitro-isophthalic acid (31.0% Zn/; 19.1% Pb) | 83 | 1 | 2 |
| 1.15 | zinc potassium chromate, lead containing acc'g to DIN 55902 | 70 | 0 | 0 |
| 1.16 | barium sulfate (i.e., zinc phosphate alone) | 55 | 0 | 0 |

(CV = corrosion protection value)

The PVC values (pigment volume concentration) of the corrosion protective coatings of Examples 1 to 16 is in the range of from 39.4 to 39.8%.

These examples of the formulation of Example 1 show the excellent corrosion-inhibiting effect of the salts of mercaptopyridine as well as those of mercapto-benzothiazole. Especially of note are the salts of mercaptobenzothiazole, as they show excellent activity at remarkably low contents of lead or zinc. Thus, the lacquer composition with 2.3% by weight mercapto-benzothiazole salt contains, in the case of the lead salt (37.3% Pb), only 0.86% lead and in the case of the zinc salt (16.4% Zn), only 0.38% zinc, when the small lead and/or zinc content of the other components of the binder formula are disregarded.

EXAMPLE 2

Composition of the binder base used:

| Parts by Weight | |
|---|---|
| 34.0 | short oil, resin modified alkyd resin with 44% linseed oil/wood oil, 60% solution in xylene |
| 9.0 | xylene |
| 5.6 | benzine, b.p. 145°–200° C. |
| 2.3 | ethylene glycol ethyl ether |
| 2.3 | Decalin ® |
| 0.2 | calcium naphthenate, (4% Ca) |
| 0.4 | cobalt naphthenate, (6% Co) |
| 0.1 | lead naphthenate, (24% Pb) |
| 0.3 | methyl ethyl ketoxime |
| 6.8 | titanium dioxide, Rutile |
| 4.5 | micro talc |
| 23.7 | barium sulfate |
| 8.5 | zinc phosphate |
| 97.7 parts by weight | Lacquer base |

To each 97.7 part portion of lacquer base were added 2.3 parts by weight each of the corrosion inhibitors tested. The Examples 2.1 to 2.7 are the salts according to the invention. Examples 2.8 to 2.11 show inhibitors according to the current state of the art. In Example 2.11, zinc phosphate is present without any additional inhibitor.

| Example | Corrosion Inhibitor | CV in % | Sediment 3 days | after- 21 days |
|---|---|---|---|---|
| 2.1 | zinc trithiocyanurate (34.2% Zn) | 83 | 0 | 0 |
| 2.2 | lead trithiocyanurate (55.6% Pb) | 90 | 0 | 0 |
| 2.3 | zinc-lead cyanurate (61.2% Pb; 3.9% Zn) | 85 | 0 | 0 |
| 2.4 | lead cyanurate (66.1% Pb) | 90 | 0 | 0 |
| 2.5 | zinc cyanurate (31.7% Zn) | 80 | 0 | 0 |
| 2.6 | thioammeline, lead salt (41.2% Pb) | 78 | 0 | 0 |
| 2.7 | thioammeline, zinc salt (18.9% Zn) | 73 | 0 | 0 |
| 2.8 | zinc salt of 5-nitro-isophthalic acid (44.1% Zn) | 73 | 2 | 4 |
| 2.9 | zinc/lead salt of 5-nitro isophthalic acid (31.0% Zn; 19.1% Pb) | 83 | 1 | 2 |
| 2.10 | zinc potassium chromate containing lead acc'g to DIN 55 902 | 70 | 0 | 0 |
| 2.11 | barium sulfate (i.e., zinc phosphate alone) | 55 | 0 | 0 |

(CV = corrosion protection value)

EXAMPLE 3

A binder base formulation analogous to Example 1 was used, omitting the zinc phosphate. Composition:

| Parts by Weight | |
|---|---|
| 34.1 | short oil, resin modified alkyd resin with 44% linseed/wood oil, 60% solution in xylene |
| 9.1 | xylene |
| 5.7 | benzine, b.p. 145° to 200° C. |
| 2.3 | ethylene glycol ethyl ether |
| 2.3 | Decalin ® |
| 0.2 | calcium napththenate, 4% Ca |
| 0.4 | cobalt naphthenate, 6% Co |
| 0.1 | lead naphthenate, 24% Pb |
| 0.3 | methyl ethyl ketoxime |
| 9.1 | titanium dioxide, Rutile |
| 9.1 | micro talc |
| 25.0 | barium sulfate |
| 97.7 | lacquer base |

To each 97.7 parts of this lacquer, 2.3 parts by weight of the tested corrosion inhibitors were added. The Examples 3.1 and 3.2 are salts according to this invention. Examples 3.3 and 3.4 are comparison compounds of the prior art.

| Example | Corrosion Inhibitor | CV in % | Sediment 3 days | after- 21 days |
|---|---|---|---|---|
| 3.1 | lead cyanurate (66.1% Pb) | 83 | 0 | 0 |
| 3.2 | zinc cyanurate (31.7% Zn) | 73 | 0 | 0 |
| 3.3 | zinc/lead salt of 5-nitro isophthalic acid (31.0% Zn: 19.1% Pb) | 75 | 1 | 2 |
| 3.4 | zinc potassium chromate, containing lead acc'g to DIN 55 902 | 50 | 0 | 0 |

The PVC values (pigment volume concentration) of the corrosion protective coatings of Examples 2 and 3 lay in the range of from 39.4 to 39.8%. The effect of an improved sedimentation behavior obtained with the corrosion protection coatings according to the invention is shown in the following examples using two additional binder formulations, where the anti-sedimentation effect of the s-triazine salts according to the invention is apparent.

| Parts by Weight | |
|---|---|
| 400 | epoxy resin-ricinen acid ester with a fatty acid content of 42%, 60% solution in xylene |
| 110 | zinc phosphate |
| 120 | micro talc |
| 80 | titanium dioxide, Rutile |
| 193.5 | barium sulfate |
| 15 | ethylene glycol ethyl ether |
| 15 | n-butanol |
| 30 | tetralin |
| 110 | higher aromatics |
| 110 | unplasticized urea resin, 65% solution in n-butanol |
| 200 | xylene |
| 1373.5 | coating base |

To each 1373.5 parts base, 26.5 parts per weight each of the subsequently mentioned corrosion inhibitors were added. In Example 4.4, zinc phosphate without any additional inhibitor was present. The pigment volume concentration (PVC) was about 34%.

| Example | Corrosion Inhibitor | Sediment after 3 | 7 | 14 | 21 | 30 | 40 days |
|---|---|---|---|---|---|---|---|
| 4.1 | zinc cyanurate (31.7% Zn) | 0 | 0 | 0 | 0 | 0 | 0 |
| 4.2 | zinc salt of nitro-iso-phthalic acid (44.1% Zn) | 3-4 | 4 | 4 | 4 | 4 | 4 |
| 4.3 | zinc/lead salt of nitro-isophthalic acid (31.0% Zn; 19.1% Pb) | 3-4 | 4 | 4 | 4 | 4 | 4 |
| 4.4 | barium sulfate, i.e., zinc phosphate by itself | 0-1 | 2 | 3-4 | 4 | 4 | 4 |

EXAMPLE 5

Composition of the air-drying base coat used:

| Parts by Weight | |
|---|---|
| 370 | linseed oil/alkyd with an oil content of 38% and modified with 20% resin, 60% solution in xylene |
| 80 | zinc phosphate |
| 110 | micro talc |
| 168 | barium sulfate |
| 60 | titanium dioxide, Rutile |
| 20 | Decalin ® |
| 15 | ethylene glycol ethyl ether |
| 1 | cobalt naphthenate, 6% Co |
| 4 | lead naphthenate, 24% lead |
| 1 | manganese naphthenate, 6% Mn |
| 56 | higher aromatics |
| 3 | methyl ethyl ketoxime |
| 190 | xylene |
| 1078 | vehicle |

To each 1078 parts of this vehicle were added 22 parts by weight each of the tested corrosion inhibitors. In Example 5.3, zinc phosphate without any additional inhibitor was present. The pigment volume concentration (PVC) was about 38%.

| Example | Corrosion Inhibitor | Sediment after | | | | | |
|---------|---------------------|----|----|----|----|----|----|
| | | 3 | 7 | 14 | 21 | 30 | 40 days |
| 5.1 | zinc cyanurate (31.7% Zn) | 0 | 0 | 0 | 0 | 0 | 0-1 |
| 5.2 | zinc salt of 5-nitro isophthalic acid (44.1% Zn) | 1 | 1-2 | 2 | 2 | 2-3 | 3-4 |
| 5.3 | barium sulfate, i.e., zinc phosphate by itself | 0 | 0 | 0 | 0 | 0 | 0-1 |

EXAMPLE 6

Regarding the proven improvement in the sedimentation behavior of the corrosion protection coatings by the salts according to the invention, the median particle diameter d of some of the corrosion inhibitors used, was determined by means of the so-called Coulter Counter apparatus. This device works according to a process where a dilute, electrically conductive suspension flows through an aperture (20 to 400 μm). At the passage of a particle through this aperture, the electric conductivity changes proportionally to the volume of the particle. The impulses so obtained are counted and analyzed as to their magnitude (see H. Kittel, *Textbook of Lacquers and Coatings*, Vol. II, Colomb (Berlin 1974), page 512, as well as T. C. Patton, *Pigment Handbook*, Vol. III, Wiley (New York 1973), pages 101-106).

The following values were obtained:

| Corrosion Inhibitor | Median particle diameter d in μm |
|---------------------|----------------------------------|
| zinc cyanurate (31.7% Zn) | 10.0 |
| zinc mercaptobenzothiazole (16.4% Zn) | 9.5 |
| zinc salt of 5-nitroisophthalic acid (44.1% Zn) | 5.0 |
| zinc/lead salt of 5-nitro isophthalic acid (31.0% Zn; 19.1% Pb) | 8.5 |

The surprisingly good anti-sedimentation effect of zinc cyanurate as well as of zinc mercaptobenzothiazole is therefore not conditional on the particle size, since all determined values for d lie at the same magnitude.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. The method of providing corrosion resistance to a metal object which comprises the steps of applying to said object a layer of a corrosion-protective composition which contains a corrosion-protecting amount of at least one zinc and/or lead salt selected from the group consisting of zinc, lead and mixed lead/zinc salts of mercaptobenzothiazoles, mercaptopyridines, single or polynuclear-s-triazines containing at least one hydroxyl or mercapto group on the triazine ring, cyanuric acid and thiocyanuric acid, in a film-forming vehicle, and then drying said layer to form a continuous coating thereon.

2. The method of claim 1 wherein said salt is present in said vehicle in a concentration of range of substantially 0.5% to 10% by weight.

3. The method of claim 2 wherein said salt concentration range is 1% to 3% by weight.

4. The method of claim 1 wherein said salt is selected from the group consisting of the zinc, lead and mixed lead/zinc salts of
hydantoin,
2,4-dithiohydantoin,
2-mercaptothiazole,
2-mercapto-4-hydroxythiazole,
2-mercaptobenzoxazole,
2-mercaptobenzothiazole,
2-mercaptopyridine,
3-cyano-6-hydroxy-4-methylpyridone-2,
barbituric acid,
5-nitroorotic acid,
uric acid
guanine,
xanthine,
cyanuric acid,
monothiocyanuric acid,
dithiocyanuric acid,
2,4,6-trimercapto-s-triazine,
2,4-dihydroxy-s-triazine,
ammelide,
monothioammelide,
2,4-dimercapto-6-amino-s-triazine,
ammeline,
thioammeline,
acetothioguanide,
acetoguanamide,
o-carboxybenzoguanide,
oxonic acid,
2-hydroxy-4,6-dimethoxy-s-triazine,
2,4-dihydroxy-6-(p-nitrophenyl)-s-triazine,
2,4-dihydroxy-6-allyloxy-s-triazine,
and
cyameluric acid.

5. The method of claim 1 wherein said vehicle includes, as the film-forming component, a polymeric resin selected from the group consisting of alkyd resins, epoxy resins and urethane resins.

6. The method of claim 1 wherein the continuous coating is from substantially 10 to 100 μm thick.

7. A corrosion-protected metal object having a continuous coating applied in accordance with the method of claim 1.

* * * * *

UNITED STATES PATENT AND TRADEMARK OFFICE
CERTIFICATE OF CORRECTION

PATENT NO. : 4,329,381
DATED : May 11, 1982
INVENTOR(S) : HELMUT ESCHWEY et al.

It is certified that error appears in the above—identified patent and that said Letters Patent is hereby corrected as shown below:

Column 10, after line 4, please insert

-- Example 4

Composition of the primer based on an epoxy resin --.

Signed and Sealed this

Twenty-sixth Day of October 1982

[SEAL]

Attest:

Attesting Officer

GERALD J. MOSSINGHOFF
Commissioner of Patents and Trademarks